United States Patent [19]

Moretz et al.

[11] Patent Number: 5,249,320

[45] Date of Patent: Oct. 5, 1993

[54] MOISTURE-MANAGING BED PAD AND BED SHEET

[76] Inventors: Herbert L. Moretz, 20205 Lola Cir., Davidson, N.C. 28036; Daniel L. Brier, 33 Anglefish Cay Dr., Key Largo, Fla. 33037

[21] Appl. No.: 23,006

[22] Filed: Feb. 26, 1993

Related U.S. Application Data

[63] Continuation-in-part of Ser. No. 3,263, Jan. 12, 1993, Pat. No. 4,800,738, which is a continuation-in-part of Ser. No. 991,761, Dec. 17, 1992, which is a continuation-in-part of Ser. No. 945,677, Sep. 16, 1992, which is a continuation-in-part of Ser. No. 842,224, Feb. 26, 1992, Pat. No. 5,210,882, which is a continuation-in-part of Ser. No. 791,066, Nov. 12, 1991, Pat. No. 5,217,782.

[51] Int. Cl.$^5$ ............................................. A61F 13/15
[52] U.S. Cl. ........................................ 5/484; 5/502; 604/371; 604/378; 604/384
[58] Field of Search .................. 5/484, 487, 500, 502; 604/367, 371, 378, 381, 384

[56] References Cited

U.S. PATENT DOCUMENTS

| | | | |
|---|---|---|---|
| Re. 26,515 | 1/1969 | Holliday et al. | 604/371 X |
| 2,905,176 | 9/1959 | Davidson | 604/371 |
| 3,882,871 | 5/1975 | Taniguchi | 604/381 X |
| 3,989,867 | 11/1976 | Sisson | 5/484 X |
| 4,045,833 | 9/1977 | Mesek et al. | 5/484 |
| 4,216,774 | 8/1980 | Graber | 5/484 X |
| 4,502,156 | 3/1985 | Wichman | 604/378 X |
| 4,664,959 | 5/1987 | Dagenais et al. | 5/500 X |
| 4,723,954 | 2/1988 | Pieniak | 604/378 X |
| 4,844,965 | 7/1989 | Foxman | 5/484 X |
| 4,961,982 | 10/1990 | Taylor | 5/484 X |
| 5,099,532 | 3/1992 | Thomas et al. | 5/502 X |

*Primary Examiner*—Michael F. Trettel
*Attorney, Agent, or Firm*—W. Thad Adams, III

[57] ABSTRACT

A moisture-managing bed pad and bed sheet are provided for being positioned between a patient and a supporting surface. The bed sheet includes a moisture-managing bed pad. The bed pad includes a moisture transport top fabric layer for residing in patient contact and for wicking moisture away from the body of the patient. A moisture dispersal intermediate fabric layer resides adjacent the top fabric layer for receiving and dispersing moisture from the top fabric layer, and for providing a reservoir for moisture wicked inwardly from the top fabric layer. A liquid impermeable, vapor permeable bottom fabric layer resides adjacent to the intermediate fabric layer for providing a leak-proof barrier. The barrier permits dissipation of moisture in vapor form. The top, intermediate, and bottom fabric layers of the bed pad are attached by spot welds to form a unitary structure. One or more sheet sections reside adjacent to the bed pad for defining the bed sheet.

22 Claims, 2 Drawing Sheets

MOISTURE-MANAGING BED PAD AND BED SHEET

TECHNICAL FIELD AND BACKGROUND OF THE INVENTION

This application is a continuation-in-part of application Ser. No. 003,263, filed on Jan. 12, 1993, now U.S. Pat. No. 4,800,738, which is a continuation-in-part of application Ser. No. 991,761, filed on Dec. 17, 1992, still pending, which is a continuation-in-part of Ser. No. 945,677, filed on Sep. 16, 1992, still pending, which is a continuation-in-part of Ser. No. 842,224, filed on Feb. 26, 1992, now. U.S. Pat. No. 5,210,882 which is a continuation-in-part of application Ser. No. 791,066, filed on Nov. 12, 1991 now U.S. Pat. No. 5,217,782.

The invention relates to a moisture-managing bed pad and bed sheet. The bed pad includes multiple layers of fabric suitably attached, and designed to wick and disperse moisture away from the body of a patient. The fabric layers are further designed to allow retained moisture to dissipate from the bed pad in vapor form, while preventing moisture leakage out of the pad and onto the mattress or other surface.

The bed sheet incorporates the moisture-managing bed pad with one or more sheet sections constructed of a particular bi-component fabric. The bi-component fabric forms the surface layer of the bed pad and sheet. The effect of the bed pad and bed sheet is to keep the body of the patient as dry as possible, while preventing the mattress or other supporting surface from becoming wet from urine or perspiration seepage through the bed pad or sheet.

As the population in the United States and most other countries ages, increasingly large numbers of people world wide are hospitalized or spend long periods in convalescent care and nursing home facilities. This invention addresses two major problems faced by those facilities: (1) varying degrees of urinary incontinence experienced by a high percentage of patients (half of those in nursing homes, according to recently published estimates) ; and (2) pressure sores, rashes and chafing resulting from prolonged confinement in bed.

In some cases, perhaps many, the urinary incontinence problem may be a causative factor for bed sores among nursing home patients who, because of staff shortages, may lie unattended for long periods of time. This could lead to further health problems.

Presently, a bed pad of cotton fabric bonded to butyl rubber is in widespread use in hospitals and nursing care facilities. This type of bed pad is waterproof, but two characteristics of its components create conditions that can be improved upon. First, cotton fibers absorb moisture into the structure of the fiber itself, and thus hold wetness next to the body. Secondly, the rubber does not allow the moisture underneath the patient's body to be wicked away from the skin or to evaporate readily.

Thus, a rubber bed pad, even when coated with cotton fibers, tends to prevent the dissipation of moisture from the body, and therefore contributes to a condition of uncomfortable warmth and perspiration. This may exacerbate a patient's discomfort and contribute to added perspiration wetness, for example, in cases of high fever.

It is clear that moisture and lack of air flow are major contributing factors to pressure sores and other skin disorders associated with long-term confinement in bed. The bed pad and sheet, according to this invention, is designed to create a healthier, dry environment next to a patient's body by managing and protecting other bedding from moisture arising from urinary leakage or perspiration.

SUMMARY OF THE INVENTION

Therefore, it is an object of the invention to provide a moisture-managing bed pad and bed sheet which are constructed from an integral multi-layer fabric which has moisture-management characteristics.

It is another object of the invention to provide a moisture-managing bed pad and bed sheet including an integral multi-layer fabric designed for wicking moisture from the body, transferring the moisture to inner layers, and ultimately allowing the moisture to dissipate in vapor form.

It is another object of the invention to provide a moisture-managing bed pad and bed sheet constructed of an integral multi-layer fabric which can be used to cover any given surface, such as an automobile driver's seat, a wheelchair, or an operating table.

It is another object of the invention to provide a moisture-managing bed pad and bed sheet which provides a dry surface and healthier environment for a patient confined to a bed.

It is another object of the invention to provide a moisture-managing bed pad and bed sheet which is constructed of a multi-layer fabric which has adjacent layers of hydrophobic and hydrophilic fabrics which exert a simultaneous push-pull effect on moisture to thereby move the moisture from one side of the adjacent layers to the other side. One of the fabric layers of the bed pad and bed sheet is itself formed of two integrally-formed fabric layers.

It is another object of the invention to provide a moisture-managing bed pad constructed of a multi-layer fabric which incorporates one or more layers which are moisture vapor permeable and liquid impermeable.

It is another object of the invention to provide a moisture-managing bed pad which has multiple moisture-managing fabrics which are overlaid and attached by spot welds throughout the surface area of the bed pad.

These and other objects of the present invention are achieved in the preferred embodiments disclosed below by providing a moisture-managing bed pad for being positioned between a patient and a supporting surface. The bed pad includes a moisture transport top fabric layer for residing in patient contact and for wicking moisture away from the body of the patient. A moisture dispersal intermediate fabric layer resides adjacent the top fabric layer for receiving and dispersing moisture from the top fabric layer, and for providing a reservoir for moisture wicked inwardly from the top fabric layer. A liquid impermeable, vapor permeable bottom fabric layer resides adjacent to the intermediate fabric layer for providing a leak-proof barrier. The barrier permits dissipation of moisture in vapor form. The top, intermediate, and bottom fabric layers are attached together to form a unitary structure.

According to one preferred embodiment of the bed pad, the top fabric layer is constructed of a "push-pull" integrated knit fabric having hydrophobic yarn on an outer fabric face thereof for residing in patient contact, and having hydrophilic yarn on an inner fabric face in surface contact with the intermediate fabric layer.

According to another preferred embodiment of the bed pad, the hydrophobic yarn of the outer face of the top fabric layer is chosen from the fiber group consisting of polyester and polypropylene.

Preferably, the hydrophobic yarn of the outer face of the top fabric layer is formed of fibers having a high surface area in relation to volume.

According to yet another preferred embodiment of the bed pad, the hydrophilic yarn of the inner face of the top fabric layer is chosen from the fiber group consisting of hydrophilic nylon, cotton, rayon and blends of hydrophilic nylon and conventional nylon.

According to yet another preferred embodiment of the bed pad, the intermediate fabric layer of the bed pad is constructed of hydrophilic yarn chosen from the fiber group consisting of hydrophilic nylon, cotton, rayon and blends of hydrophilic nylon and conventional nylon.

According to yet another preferred embodiment of the bed pad, the bottom fabric layer of the bed pad is constructed of yarn chosen from the fiber group consisting of polyester and nylon microfiber.

According to yet another preferred embodiment of the bed pad, the attachment means for attaching the fabric layers includes spot welds joining at least two of the top, intermediate, and bottom fabric layers.

Preferably, the spot welds are spaced apart in ranks and files at predetermined intervals throughout the surface area of the bed pad.

According to yet another preferred embodiment of the bed pad, the spot welds include a concentrated weld bead with a peripheral area of substantially less concentration.

According to yet another preferred embodiment of the bed pad, the attachment means further includes stitching together at least two of the respective perimeters of the top, intermediate, or bottom fabric layers.

A moisture-managing bed sheet, according to one preferred embodiment of the invention, is provided by incorporating a moisture-managing bed pad as described above and a sheet section. The bed pad includes a moisture transport top fabric layer for residing in patient contact and for wicking moisture away from the body of the patient. A moisture dispersal intermediate fabric layer resides adjacent the top fabric layer for receiving and dispersing moisture from the top fabric layer, and for providing a reservoir for moisture wicked inwardly from the top fabric layer. A liquid impermeable, vapor permeable bottom fabric layer resides adjacent to the intermediate fabric layer for providing a leak-proof barrier. The barrier permits dissipation of moisture in vapor form. The top, intermediate, and bottom fabric layers are attached together to form a unitary structure. One or more sheet sections are attached to and extend outwardly from the bed pad.

According to another preferred embodiment of the bed sheet, the top fabric layer of the bed pad is constructed of a "push-pull" integrated knit fabric having hydrophobic yarn on an outer fabric face thereof for residing in patient contact, and having hydrophilic yarn on an inner fabric face in surface contact with the intermediate fabric layer of the bed pad.

According to yet another preferred embodiment of the bed sheet, the hydrophobic yarn of the outer face of the top fabric layer of the bed pad is chosen from the fiber group consisting of polyester and polypropylene.

Preferably, the hydrophobic yarn of the outer face of the top fabric layer of the bed pad is formed of fibers having a high surface area in relation to volume.

According to yet another preferred embodiment of the bed sheet, the hydrophilic yarn of the inner face of the top fabric layer of the bed pad is chosen from the fiber group consisting of hydrophilic nylon, cotton, rayon and blends of hydrophilic nylon and conventional nylon.

According to yet another preferred embodiment of the bed sheet, the intermediate fabric layer of the bed pad is constructed of hydrophilic yarn chosen from the fiber group consisting of hydrophilic nylon, cotton, rayon and blends of hydrophilic nylon and conventional nylon.

According to yet another preferred embodiment of the bed sheet, the bottom fabric layer of the bed pad is constructed of yarn chosen from the fiber group consisting of polyester and nylon microfiber.

According to yet another preferred embodiment of the bed sheet, the top, intermediate, and bottom layers of the bed pad have spot welds to attach at least two of the top, intermediate, and bottom fabric layers.

According to yet another preferred embodiment of the bed sheet, the spot welds are spaced apart at predetermined intervals in ranks and files throughout the surface area of the bed pad portion of the bed sheet.

Preferably, the spot welds include a concentrated weld bead with a peripheral area of less concentration.

According to yet another preferred embodiment of the bed sheet, at least two of the respective perimeters of the top, intermediate, or bottom fabric layers are stitched together.

According to yet another preferred embodiment of the bed sheet, the sheet section is constructed of a "push-pull" integrated knit fabric having hydrophobic yarn on an outer fabric face thereof for residing in patient contact, and having hydrophilic yarn on an inner fabric face.

According to yet another preferred embodiment of the bed sheet, the hydrophobic yarn of the outer face of the sheet section is chosen from the fiber group consisting of polyester and polypropylene.

Preferably, the hydrophobic yarn of the outer face of the sheet section is formed of fibers having a high surface area in relation to volume.

According to yet another preferred embodiment of the bed sheet, the hydrophilic yarn of the inner face of the sheet section is chosen from the fiber group consisting of hydrophilic nylon, cotton, rayon and blends of hydrophilic nylon and conventional nylon.

According to yet another preferred embodiment of the bed sheet, the sheet section is integrally formed to the top fabric layer of the bed pad, and extends outward from the bed pad to substantially comprise the sheet section.

According to yet another preferred embodiment of the bed sheet, the moisture-managing bed sheet further includes fitting means for securing a perimeter portion of the bed sheet to a mattress, and for keeping the bed sheet in a relatively fixed position on the mattress.

According to one preferred embodiment of the invention, a moisture-managing bed sheet is provided for being positioned between a patient and a mattress. The bed sheet includes a moisture-managing bed pad. The bed pad includes a moisture transport top fabric layer for residing in patient contact and for wicking moisture away from the body of the patient. A moisture dispersal intermediate fabric layer resides adjacent to the top fabric layer for receiving and dispersing moisture from the top fabric layer, and for providing a reservoir for moisture wicked inwardly from the top fabric layer. A liquid impermeable, vapor permeable bottom fabric layer resides adjacent to the intermediate fabric layer for providing a leak-proof barrier. The barrier permits dissipation of moisture in vapor form. An attachment means attaches the top, intermediate, and bottom fabric layers to form a unitary structure. One or more sheet sections reside adjacent to the bed pad for defining the bed sheet. A fitting means secures a perimeter portion of the bed sheet to a mattress, and keeps the bed pad in a relatively fixed position.

BRIEF DESCRIPTION OF THE DRAWINGS

Some of the objects of the invention have been set forth above. Other objects and advantages of the invention will appear as the invention proceeds when taken in conjunction with the following drawings, in which.

DESCRIPTION OF THE PREFERRED EMBODIMENT AND BEST MODE

Figure 1:
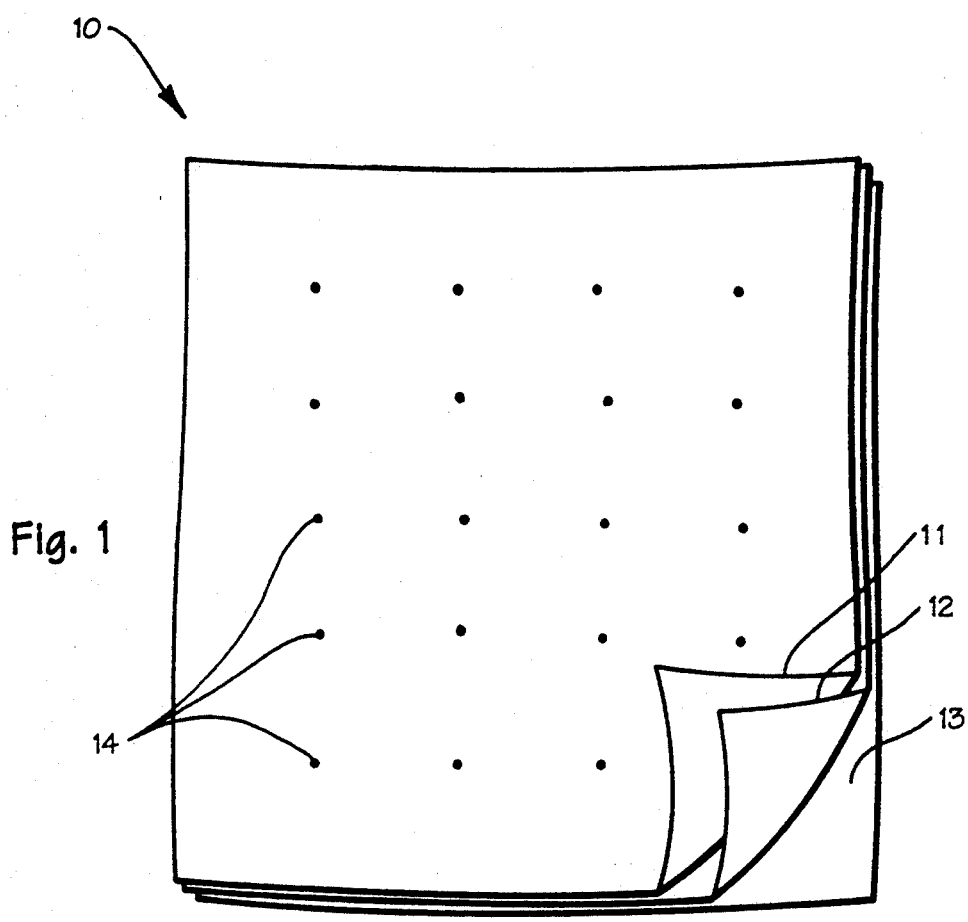
FIG. 1 is a moisture-managing bed pad according to an embodiment of the present invention.
Figure 4:
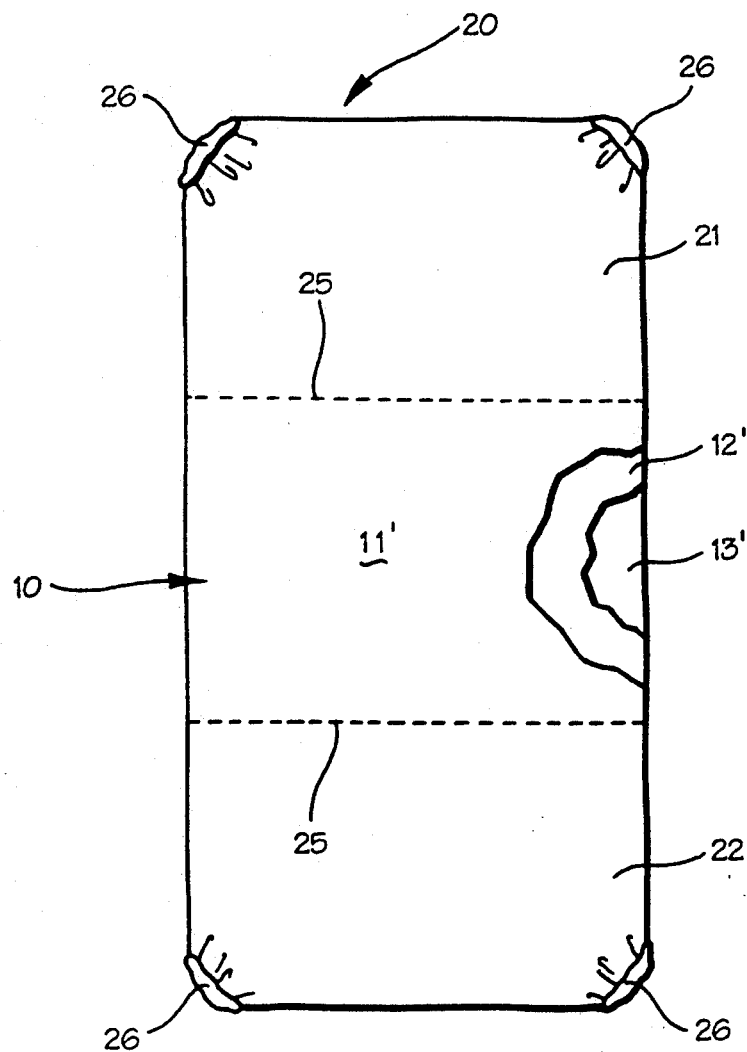
FIG. 4 is a moisture-managing bed sheet according to an embodiment of the present invention.

Referring now specifically to the drawings, a moisture-managing bed pad according to the present invention is illustrated in FIG. 1 and shown generally at reference numeral 10. A moisture-managing bed sheet, which includes a bed pad 10', is illustrated in FIG. 4 and shown generally at reference numeral 20. Both the bed pad 10 and the bed sheet 20 are launderable and reusable.

Moisture-Managing Bed Pad

Figure 2:
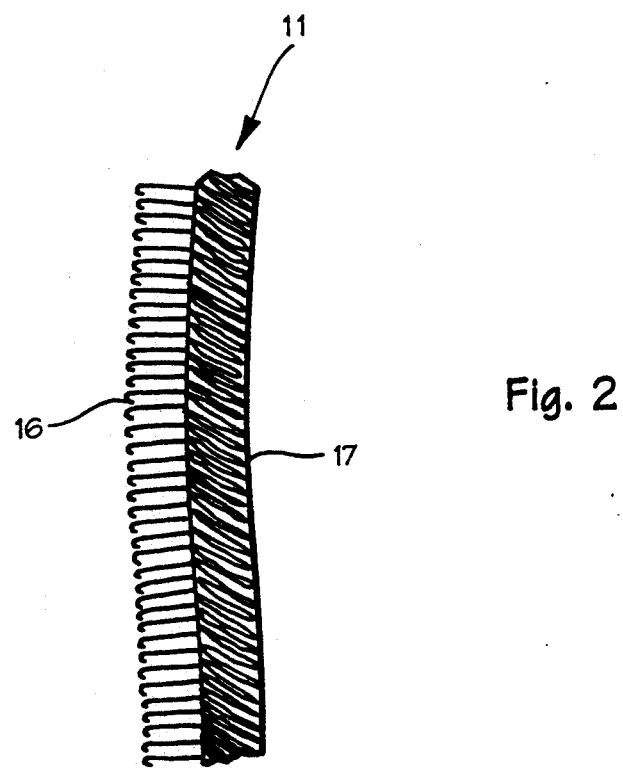
FIG. 2 is a cross-sectional view of a "push-pull" knit fabric shown in FIG. 1 that integrates hydrophobic fibers and hydrophilic fibers according to an embodiment of the invention.

According to a preferred embodiment shown in FIG. 1, the bed pad 10 is approximately 36 inches in length and width, and includes top, intermediate, and bottom fabric layers 11, 12, and 13, respectively. The top fabric layer 11 is the uppermost fabric layer of the bed pad 10, or the layer which resides in direct contact with the body of the patient. As shown in FIG. 2, this layer is constructed of an integrally-knit, bi-component fabric having outer and inner fabric faces, 16 and 17, respectively.

The outer fabric face 16 is preferably constructed of hydrophobic polyester fibers which comprise the outermost surface of the bed pad 10, and which reside in contact with the patient's body or skin. According to another embodiment, the hydrophobic fibers of the outer fabric face 16 are chosen from the polypropylene fiber group.

Preferably, the non-absorbent, hydrophobic fibers of the outer face 16 are brushed or napped to facilitate their ability to remove moisture from the patient's body. The configuration of the hydrophobic fiber affords a relatively large surface area having longitudinal channels designed to more effectively transport or wick moisture away from the source of body heat. Consequently, one function of the outer fabric face 16 of the top fabric layer 11 is to transfer moisture away from the body of the patient, and thereby disperse the moisture within the inner layers of the bed pad 10. This will provide a more comfortable and drier fabric surface next to the body or skin of the patient.

The integrally-knit inner fabric face 17 of the top fabric layer 11 is preferably constructed of hydrophilic nylon fibers. These nylon fibers are designed to receive and disperse moisture wicked inwardly by the hydrophobic fibers of the outer fabric face 16. The hydrophilic fibers are preferably chosen from the fiber group consisting of hydrophilic nylon, cotton, rayon and blends of hydrophilic nylon and conventional nylon.

The bi-component nature of the outer and inner fabric faces 16 and 17 of the first fabric layer 11 creates a "push-pull" effect on moisture passing from the outer fabric face 16 to the inner fabric face 17. The top fabric layer 11 causes moisture to be pushed by body heat along the hydrophobic fibers of the outer fabric face 16, and then pulled inwardly by the integrated hydrophilic fibers of the inner fabric face 17.

The intermediate fabric layer 12 resides adjacent to and in surface contact with the hydrophilic inner face 17 of top fabric layer 11. The intermediate layer 12 is constructed of hydrophilic fibers, and thus acts to further receive and disperse moisture wicked inwardly from the top fabric layer 11. Moreover, the intermediate fabric layer 12 functions as a reservoir for holding substantial quantities of moisture. This serves to enhance the overall ability of the bed pad 10 to maintain a relatively dry fabric surface next to the body of the patient.

Preferably, the bottom fabric layer 13 is constructed of a polyester microfiber fabric that is liquid impermeable, but moisture vapor permeable and breathable. The bottom fabric layer 13 is designed to provide a leak-proof barrier which protects the bedding from liquid, while allowing moisture in vapor form to pass through and dissipate. According to another preferred embodiment, the bottom fabric layer 13 is constructed of nylon microfibers, i.e., fibers having less than 1.0 denier per filament.

Figure 3:
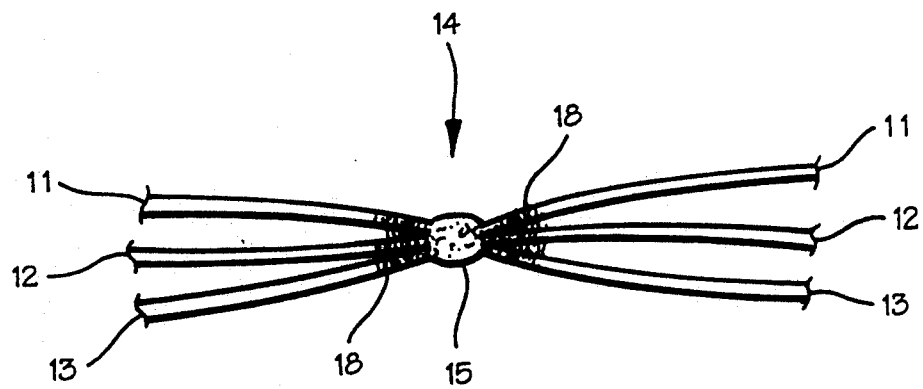
FIG. 3 is a partial cross-sectional view of the invention showing a spot weld for attaching the top, intermediate, and bottom layers of the invention.

As is shown in FIG. 1, the fabric layers are attached by spot welds 14 spaced throughout the surface of the bed pad 10. The spot welds 14 are preferably formed by an ultrasonic heat applicator which heats two or more of the top, intermediate, or bottom fabric layers 11, 12, and 13, respectively, to produce a small, concentrated weld bead 15. As shown in FIG. 3, the weld bead 15 includes a peripheral area 18 where the fabric layers are only partially fused together. This type of attachment produces a stronger, more effective bonding of the fabric layers without creating areas of stress at the boundary between fused and unfused fibers. This is accomplished by using an ultrasonic head having a convex profile.

Additionally, the spot welds 14 provide stability to the bed pad 10, and wrinkle free use of the bed pad 10. According to one embodiment, the fabric layers 11, 12 and 13 are spot welded in ranks and files such as illustrated in FIG. 1. This method of attachment is preferable since it avoids needle holes in the fabric layers, thus retaining the liquid impermeability of the bottom fabric layer 13. To further complete the attachment of the fabric layers, the bed pad 10 can be finished along its perimeter either by sewing the side edges of the layers together using an over-edge or other standard stitch formation, or by ultrasonic bonding. According to another preferred embodiment of the invention, the fabric layers are attached solely by sewing the side edges of the layers together using an over-edge or other standard stitch formation, or by ultrasonic bonding.

The multi-layer system of the present invention allows air flow in and out through both the top and bottom fabric layers, 11 and 13. This feature enhances evaporation of moisture, and may thus retard the growth of bacteria that can be harmful to the skin of the patient.

Other potential uses of the bed pad, according to the present invention, include wheelchair pads, pads for operating tables, pads for infant cribs, pads for truck drivers, buses and automobiles, operators of heavy equipment, and others who sit for long periods on vinyl or rubberized surfaces.

Moisture-Managing Bed Sheet

FIG. 4 illustrates a moisture-managing bed sheet 20, which includes the moisture-managing bed pad 10' and one or more sheet sections 21 and 22. The bed sheet 20, according to the present invention, can be manufactured to fit beds or children's cribs of any size. According to one preferred embodiment, the bed pad 10' is positioned in the center portion of the bed sheet 20 and flanked by sheet sections 21 and 22. Prime notation indicates a structure like that of bed pad 10, described above.

Preferably, a top fabric layer 11' of the bed pad 10' extends the full length and width of the bed sheet 20, and thus comprises sheet sections 21 and 22. The sheet sections 21 and 22, and the top layer 11' of the bed pad 10', are constructed of an integrally-knit, bi-component fabric having an outer hydrophobic face and an inner hydrophilic face.

The intermediate and bottom fabric layers 12' and 13' of the bed pad 10' are bonded ultrasonically at respective perimeter edges to the bed sheet 20. As shown in FIG. 4, this bond comprises a thin, broken-line weld 25 for securing the bed pad 10' to the bed sheet 20. According to another preferred embodiment, the sheet sections 21 and 22 are attached to the bed pad 10' by sewing the adjacent perimeter edges of the sheet sections 21 and 22 to the layers 12' and 13' of the bed pad 10' using an over-edge or other standard stitch formation, or by ultrasonic bonding.

Preferably, the bed sheet 20 has "fitted" sheet corners 26 reinforced with elastic to provide a secure, wrinkle-free fit and to ensure that the moisture-managing bed pad 10' remains properly located in the center of the mattress at all times. The bed sheet 20 is hemmed along its perimeter, including the section incorporating the bed pad 10', in a manner similar to conventional bed sheets.

A moisture-managing bed pad and bed pad sheet according to the present invention are described above. Various details of the invention may be changed without departing from its scope. Furthermore, the foregoing description of the preferred embodiment of the invention is provided for the purpose of illustration only and not for the purpose of limitation—the invention being defined by the claims.

I claim:

1. A moisture-managing bed pad for being positioned between a patient and a supporting surface, comprising:
    (a) a moisture transport top fabric layer for residing in patient contact and for wicking moisture away from the body of the patient;
    (b) a moisture dispersal intermediate fabric layer residing adjacent said top fabric layer for receiving and dispersing moisture from said top fabric layer, and for providing a reservoir for moisture wicked inwardly from said top fabric layer;
    (c) a liquid impermeable, vapor permeable bottom fabric layer residing adjacent to said intermediate fabric layer for providing a leak-proof barrier, said barrier permitting dissipation of moisture in vapor form; and
    (d) attachment means for attaching said top, intermediate, and bottom fabric layers to form a unitary structure, wherein said attachment means comprises spot welds joining at least two of said top, intermediate, and bottom fabric layers, said spot welds spaced apart as predetermined intervals throughout the surface area of said bed pad, and including a concentrated weld bead of completely fused fibers with a peripheral area of partially fused fibers to reduce stress on edge areas of the spot welds.

2. A moisture-managing bed pad according to claim 1, wherein said top fabric layer is constructed of a "push-pull" integrated knit fabric having hydrophobic yarn on an outer fabric face thereof for residing in patient contact, and having hydrophilic yarn on an inner fabric face in surface contact with said intermediate fabric layer.

3. A moisture-managing bed pad according to claim 2, wherein the hydrophobic yarn of the outer face of said top fabric layer is chosen from the fiber group consisting of polyester and polypropylene.

4. A moisture-managing bed pad according to claim 3, wherein the hydrophobic yarn of the outer face of said top fabric layer is formed of fibers having a high surface area in relation to volume.

5. A moisture-managing bed pad according to claim 2, wherein the hydrophilic yarn of the inner face of said top fabric layer is chosen from the fiber group consisting of hydrophilic nylon, cotton, rayon and blends of hydrophilic nylon and conventional nylon.

6. A moisture-managing bed pad according to claim 1, wherein the intermediate fabric layer is constructed of hydrophilic yarn chosen from the fiber group consisting of hydrophilic nylon, cotton, rayon and blends of hydrophilic nylon and conventional nylon.

7. A moisture-managing bed pad according to claim 1, wherein the bottom fabric layer is constructed of yarn chosen from the fiber group consisting of polyester and nylon microfiber.

8. A moisture-managing bed pad according to claim 1, wherein said attachment means further includes stitches as for stitching together at least two of the respective perimeters of said top, intermediate, or bottom fabric layers.

9. A moisture-managing bed sheet, comprising:
    (a) a moisture-managing bed pad, comprising:
        (1) a moisture transport top fabric layer for residing in patient contact and for wicking moisture away from the body of the patient;
        (2) a moisture dispersal intermediate fabric layer residing adjacent said top fabric layer for receiving and dispersing moisture from said top fabric layer, and for providing a reservoir for moisture wicked inwardly from said top fabric layer;
        (3) a liquid impermeable, vapor permeable bottom fabric layer residing adjacent to said intermediate fabric layer for providing a leak-proof barrier, said barrier permitting dissipation of moisture in vapor form; and (4) attachment means for attaching said top, intermediate, and bottom fabric layers to form a unitary structure, wherein said attachment means comprises spot welds joining at least two of said top, intermediate, and bottom fabric layers, said spot welds spaced apart at predetermined intervals throughout the surface area of said bed pad, and including a concentrated weld bead of completely fused fibers with a peripheral area of partially fused fibers to reduce stress on edge areas of the spot welds; and (b) one or more sheet sections adjacent to and extending outward from said bed pad for defining said bed sheet.

10. A moisture-managing bed sheet according to claim 9, wherein said top fabric layer of the bed pad is constructed of a "push-pull" integrated knit fabric having hydrophobic yarn on an outer fabric face thereof for residing in patient contact, and having hydrophilic yarn on an inner fabric face in surface contact with the intermediate fabric layer of the bed pad.

11. A moisture-managing bed sheet according to claim 10, wherein the hydrophobic yarn of the outer face of said top fabric layer of the bed pad is chosen from the fiber group consisting of polyester and polypropylene.

12. A moisture-managing bed sheet according to claim 11, wherein the hydrophobic yarn of the outer face of said top fabric layer of the bed pad is formed of fibers having a high surface area in relation to volume.

13. A moisture-managing bed sheet according to claim 10, wherein the hydrophilic yarn of the inner face of said top fabric layer of the bed pad is chosen from the fiber group consisting of hydrophilic nylon, cotton, rayon and blends of hydrophilic nylon and conventional nylon.

14. A moisture-managing bed sheet according to claim 9, wherein the intermediate fabric layer of the bed pad is constructed of hydrophilic yarn chosen from the fiber group consisting of hydrophilic nylon, cotton, rayon and blends of hydrophilic nylon and conventional nylon.

15. A moisture-managing bed sheet according to claim 9, wherein the bottom fabric layer of the bed pad is constructed of yarn chosen from the fiber group consisting of polyester and nylon microfiber.

16. A moisture-managing bed sheet according to claim 9, wherein the attachment means further includes stitching together at least two of the respective perimeters of said top, intermediate, or bottom fabric layers.

17. A moisture-managing bed sheet according to claim 9, wherein the sheet section is constructed of a "push-pull" integrated knit fabric having hydrophobic yarn on an outer fabric face thereof for residing in patient contact, and having hydrophilic yarn on an inner fabric face.

18. A moisture-managing bed sheet according to claim 17, wherein the hydrophobic yarn of the outer face of the sheet section is chosen from the fiber group consisting of polyester and polypropylene.

19. A moisture-managing bed sheet according to claim 17, wherein the hydrophobic yarn of the outer face of the sheet section is formed of fibers having a high surface area in relation to volume.

20. A moisture-managing bed sheet according to claim 17, wherein the hydrophilic yarn of the inner face of the sheet section is chosen from the fiber group consisting of hydrophilic nylon, cotton, rayon and blends of hydrophilic nylon and conventional nylon.

21. A moisture-managing bed sheet according to claim 9, wherein the sheet section is integrally formed to the top fabric layer of the bed pad, said top fabric layer extending outward from said bed pad to substantially comprise said sheet section.

22. A moisture-managing bed sheet according to claim 9, further comprising a fitting means for securing a perimeter portion of said bed sheet to a mattress, and for keeping the bed pad in a fixed position on the mattress.

* * * * *